(12) United States Patent
Okada et al.

(10) Patent No.: US 7,682,773 B2
(45) Date of Patent: *Mar. 23, 2010

(54) CYANINE COMPOUND, OPTICAL RECORDING MATERIAL USING THE SAME AND OPTICAL RECORDING MEDIUM

(75) Inventors: Mitsuhiro Okada, Tokyo (JP); Toru Yano, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 315 days.

This patent is subject to a terminal disclaimer.

(21) Appl. No.: 11/791,487

(22) PCT Filed: Oct. 13, 2005

(86) PCT No.: PCT/JP2005/018852

§ 371 (c)(1),
(2), (4) Date: May 24, 2007

(87) PCT Pub. No.: WO2006/057113

PCT Pub. Date: Jun. 1, 2006

(65) Prior Publication Data

US 2008/0138740 A1   Jun. 12, 2008

(30) Foreign Application Priority Data

Nov. 25, 2004  (JP) .............................. 2004-340485

(51) Int. Cl.
G11B 7/24 (2006.01)
(52) U.S. Cl. .............................. 430/270.21; 430/270.2; 430/945; 428/64.8; 369/284
(58) Field of Classification Search .................. None
See application file for complete search history.

(56) References Cited

U.S. PATENT DOCUMENTS

| | | | |
|---|---|---|---|
| 6,306,478 B1 * | 10/2001 | Chen et al. | 428/64.1 |
| 7,316,836 B2 * | 1/2008 | Wada et al. | 428/64.1 |
| 7,425,401 B2 * | 9/2008 | Yano et al. | 430/270.21 |
| 2004/0058274 A1 * | 3/2004 | Fukuzawa et al. | 430/270.11 |
| 2004/0197705 A1 * | 10/2004 | Shimizu et al. | 430/270.2 |
| 2005/0031993 A1 * | 2/2005 | Yano et al. | 430/270.21 |
| 2007/0259294 A1 * | 11/2007 | Shigeno et al. | 430/495.1 |
| 2008/0033179 A1 * | 2/2008 | Yano et al. | 546/277.4 |
| 2008/0125524 A1 * | 5/2008 | Ishida et al. | 524/104 |
| 2008/0207918 A1 * | 8/2008 | Aoyama et al. | 548/455 |
| 2009/0054652 A1 * | 2/2009 | Yano et al. | 546/152 |

FOREIGN PATENT DOCUMENTS

| | | | |
|---|---|---|---|
| GB | 1350230 | * | 4/1974 |
| JP | 10-278426 | | 10/1998 |
| JP | 11-227331 | | 8/1999 |
| JP | 11-277904 | | 10/1999 |
| JP | 2001-506933 | | 5/2001 |
| JP | 2001-192579 | | 7/2001 |
| JP | 2002-52829 | | 2/2002 |
| JP | 2003-171571 | * | 6/2003 |
| JP | 2003-231359 | * | 8/2003 |
| JP | 2003-237240 | | 8/2003 |
| JP | 2004-216817 | | 8/2004 |

OTHER PUBLICATIONS

"Solid-phase catch, activate, and release synthesis of cyanine dyes," S.J. Mason et al., Organic Letters, 2002, vol. 4, No. 24, pp. 4261-4264.

Chinese Patent Office issued a Chinese Office Action dated Aug. 28, 2009, Application No. 2005800386858.

* cited by examiner

*Primary Examiner*—Martin J Angebranndt
(74) *Attorney, Agent, or Firm*—Young & Thompson (57) ABSTRACT

The cyanine compound of the present invention is represented by general formula (I) below and suitable as an optical recording material used in a recording layer of optical recording media on which recording and play-back are conducted with laser beam. The cyanine compound of the present invention particularly exhibits appropriate thermal decomposition behavior to attain sensitivity compatible with high-speed recording.

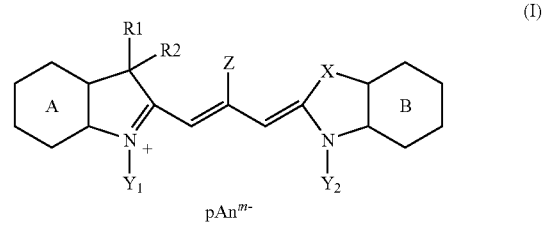

(I)

(In the formula, each of ring A and ring B represents an optionally substituted benzene or naphthalene ring; each of R1 and R2 independently represents a $C_{1-4}$ alkyl group or an optionally substituted benzyl group; at least one of R1 and R2 is an optionally substituted benzyl group; X represents O, S, or NY; each of Y, $Y_1$, and $Y_2$ independently represents a hydrogen atom or a $C_{1-30}$ organic group; Z represents a hydrogen atom, a halogen atom, or a cyano group; $An^{m-}$ represents an m-valent anion; m represents an integer of 1 or 2; and p represents a coefficient to keep an electric charge neutral.)

9 Claims, 6 Drawing Sheets

CYANINE COMPOUND, OPTICAL RECORDING MATERIAL USING THE SAME AND OPTICAL RECORDING MEDIUM

TECHNICAL FIELD

The present invention relates to a new cyanine compound, an optical recoding material comprising the cyanine compound, and optical recording medium using the optical recording material. The cyanine compound is useful as an optical element and particularly suitable for optical recording materials used in a recording layer of optical recording media on which recording and play-back are performed with laser beam. The cyanine compound can also be used as a light absorber used in optical filters of image display equipment.

BACKGROUND ART

Compounds exhibiting intense light absorption in a range of 500 to 700 nm, particularly compounds with wavelength of absorption maximum ($\lambda_{max}$) in 550 to 620 nm, are used as optical elements in optical recording layers of optical recording media such as DVD-R and in optical filters of image display equipment such as liquid crystal displays (LCD), plasma display panels (PDP), electroluminescence displays (ELD), cathode-ray tube displays (CRT), fluorescent display tubes, and field emission displays.

As the optical element, there have been studied a number of indole ring-containing cyanine compounds with highly sensitivity. A number of such cyanine compounds have been reported particularly as recording elements of optical recording media including DVD-R as a representative, owing to a merit of capability to follow speed-up of recording. For example, they are reported in Patent Documents 1 to 5 below. Patent Document 6 also describes a cyanine compound, in which a benzyl group is introduced at 3-position in the indole ring.

However, conventional cyanine compounds have a problem in thermal decomposition properties. Compounds with low decomposition temperature would be suitable as recording elements of optical recording media for high-speed recording, but the above cyanine compounds do not have sufficient properties in this aspect.

Patent Document 1: Japanese Patent Laid-Open Publication No. H10-278426
Patent Document 2: Japanese Patent Laid-Open Publication No. H11-227331
Patent Document 3: Japanese Patent Laid-Open Publication No. H11-277904
Patent Document 4: Japanese Patent Laid-Open Publication No. 2001-506933
Patent Document 5: Japanese Patent Laid-Open Publication No. 2002-52829
Patent Document 6: Japanese Patent Laid-Open Publication No. 2003-231359

DISCLOSURE OF THE INVENTION

Problems to be Solved by the Invention

Therefore, an object of the present invention is to provide a new cyanine compound exhibiting thermal behavior suitable for use in optical recording, an optical recording material containing the compound, and an optical recording medium using the optical recording material.

Means for Solving the Problems

With an idea that optimization of thermal decomposition behavior and optimization of absorption wavelength are effective to attain sensitivity compatible with high-speed recording, the present inventors have thoroughly studied and thereby found out that cyanine compounds with a specific molecular structure can solve the above problem.

The present invention is based on the above finding and provides a compound represented by general formula (I) below.

The present invention also provides an optical recording material comprising the cyanine compound and used in an optical recording layer of an optical recording media in which the optical recording layer is formed on a substrate.

The present invention also provides an optical recording medium in which a thin film made of the optical recording material is formed on a substrate.

[Formula 1]

(I)

(In the formula, each of rings A and B represents an optionally substituted benzene or naphthalene ring, each of R1 and R2 independently represents a $C_{1-4}$ alkyl groups or an optionally substituted benzyl group, and at least one of R1 and R2 is an optionally substituted benzyl group; X represents O, S, or NY, each of Y, $Y_1$, and $Y_2$ independently represents a hydrogen atom or a $C_{1-30}$ organic group; Z represents a hydrogen atom, a halogen atom, or a cyano group; $An^{m-}$ represents an m-valent anion, m represents an integer of 1 or 2; and p represents a coefficient to keep an electric charge neutral.)

BRIEF DESCRIPTION OF DRAWINGS

FIG. 1-*a* is the $^1$H-NMR spectrum of hexafluorophosphate of Compound No. 2 obtained in Example 1.
FIG. 1-*b* is one partially enlarged view of FIG. 1-*a*.
FIG. 1-*c* is another partially enlarged view of FIG. 1-*a*.
FIG. 2-*a* is the $^1$H-NMR spectrum of hexafluorophosphate of Compound No. 8 obtained in Example 2.
FIG. 2-*b* is one partially enlarged view of FIG. 2-*a*.
FIG. 2-*c* is another partially enlarged view of FIG. 2-*a*.

BEST MODES FOR CARRYING OUT THE INVENTION

The cyanine compounds of the present invention represented by general formula (I) are new compounds with a benzyl group, which may optionally have (a) substituent(s), on a specific position and have characteristics with lower decomposition temperature and more appropriate absorption wavelength than other cyanine compounds used in optical recording materials for DVD-R.

In general formula (I), the substituents in the optionally substituted benzene or naphthalene ring represented by ring A or B include halogen atoms such as fluorine, chlorine, bromine, and iodine; alkyl groups such as methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl, and 2-ethylhexyl; aryl groups such as phenyl, naphthyl, 2-methylphenyl, 3-methylphenyl, 4-methylphenyl, 4-vinylphenyl, and 3-isopropylphenyl; alkoxy groups such as methoxy, ethoxy, propoxy, isopropoxy, butoxy, sec-butoxy, and tert-butoxy; alkylthio groups such as methylthio, ethylthio, propylthio, isopropylthio, butylthio, sec-butylthio, and tert-butylthio; nitro, cyano, and the like.

In general formula (I), the $C_{1-4}$ alkyl group represented by R1 or R2 includes methyl, ethyl, propyl, isopropyl, butyl, sec-butyl, tert-butyl, isobutyl, and the like.

At least one of groups represented by R1 or R2 is an optionally substituted benzyl group. The allowable number of substituents in the benzyl group is one or two. The substituents include halogen atoms such as fluorine, chlorine, bromine, and iodine; alkyl groups such as methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl, and 2-ethylhexyl; halogen-substituted derivatives of these alkyl groups; alkoxy groups such as methoxy, ethoxy, propoxy, isopropoxy, butoxy, sec-butoxy, and tert-butoxy; halogen-substituted derivatives of these alkoxy groups; alkylthio groups such as methylthio, ethylthio, propylthio, isopropylthio, butylthio, sec-butylthio, and tert-butylthio; nitro, cyano, hydroxyl, and the like. However, since a cyanine compound with a bulky group as this substituent has a lower molar absorption coefficient, which possibly affects sensitivity, preferred substituted benzyl groups are represented by general formula (II) below:

[Formula 2]

(II)

(In the formula, m represents an integer of 1 or 2; $X_1$ represents a hydroxyl group, a halogen atom, a cyano group, a nitro group, a $C_{1-4}$ alkyl group, a $C_{1-4}$ haloalkyl group, a $C_{1-4}$ alkoxy group, or a $C_{1-4}$ haloalkoxy group; and two $X_1$s may be the same or different when m is 2.)

In general formula (II), the halogen atom represented by $X_1$ includes fluorine, chlorine, bromine, iodine and the like; the $C_{1-4}$ alkyl group includes methyl, ethyl, propyl, isopropyl, butyl, sec-butyl, tert-butyl, and isobutyl; the $C_{1-4}$ haloalkyl group includes chloromethyl, dichloromethyl, trichloromethyl, bromomethyl, dibromomethyl, tribromomethyl, fluoromethyl, difluoromethyl, trifluoromethyl, perfluoroethyl, perfluoropropyl, perfluorobutyl, and the like; the $C_{1-4}$ alkoxy group includes methoxy, ethoxy, propoxy, isopropoxy, butoxy, sec-butoxy, tert-butoxy, and the like; and the $C_{1-4}$ haloalkoxy group includes chloromethoxy, dichloromethoxy, trichloromethoxy, bromomethoxy, dibromomethoxy, tribromomethoxy, fluoromethoxy, difluoromethoxy, trifluoromethoxy, perfluoroethoxy, perfluoropropoxy, perfluorobutoxy, and the like.

In general formula (I), the $C_{1-30}$ organic group represented by $Y_1$ or $Y_2$ is not particularly limited to, but includes, for example, alkyl groups such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, and octadecyl; alkenyl groups such as vinyl, 1-methylethenyl, 2-methylethenyl, propenyl, butenyl, isobutenyl, pentenyl, hexenyl, heptenyl, octenyl, decenyl, pentadecenyl, and 1-phenylpropen-3-yl; alkylaryl groups such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenol, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, and cyclohexylphenyl; aralkyl groups such as benzyl, phenethyl, 2-phenylpropan-2-yl, diphenylmethyl, triphenylmethyl, styryl and cinnamyl; and groups in which these hydrocarbon group just recited is discontinued with (an) ether bond(s) and/or (a) thioether bond(s), for example, 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. These groups may be substituted with an alkoxy, alkenyl, nitro, or cyano group, a halogen atom, or the like.

With a bulky group as the substituent represented by $Y_1$ or $Y_2$, cyanine compounds have smaller molar absorption coefficients, which may affect the sensitivity, so that $Y_1$ and $Y_2$ are preferably $C_{1-8}$ hydrocarbon groups and more preferably $C_{1-8}$ alkyl groups.

When X is NY, the $C_{1-30}$ organic groups represented by Y includes those in $Y_1$ and $Y_2$ described above.

In general formula (I), the halogen atom represented by Z includes fluorine, chlorine, bromine, and iodine.

In general formula (I), the anion represented by $An^{m-}$ includes, for example, as a monovalent anion, halides such as chloride, bromide, iodide, and fluoride; inorganic anions such as perchlorate, chlorate, thiocyanate, hexafluorophosphate, hexafluoroantimonate, and tetrafluoroborate; organic sulfonates such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate; organic phosphate such as octylphosphate, dodecylphosphate, octadecylphosphate, phenylphosphate, nonylphenylphosphate, and 2,2'-methylenebis(4,6-di-tert-butylphenyl)phosphonate; and the like. Examples of a divalent anion include benzenedisulfonate, naphthalenedisulfonate, and the like. There may be also used, as necessary, quencher anions having function to deactivate (quench) active molecules in an excited state or anions of metallocene compounds such as ferrocene and ruthenocene having an anionic group such as a carboxyl, phosphonic acid, and sulfonic acid group on the cyclopentadienyl ring.

The quencher anions include, for example, anions represented by general formula (A) or (B) below and the anions described in Japanese Patent Laid-Open Publication No. S60-234892, Japanese Patent Laid-Open Publication No. H5-43814, Japanese Patent Laid-Open Publication No. H6-239028, Japanese Patent Laid-Open Publication No. H9-309886, Japanese Patent Laid-Open Publication No. H10-45767, and the like.

[Formula 3]

(A)

-continued (B)

(In the formulae, M represents a nickel or copper atom; R5 and R6 each represent a halogen atom, a $C_{1-8}$ alkyl group, a $C_{6-30}$ aryl group, or —$SO_2Z$; Z represents an alkyl, optionally halogenated aryl, dialkylamino, diarylamino, piperidino, or morpholino group; and a and b each represent a number of 0 to 4. Each of R7, R8, R9, and R10 independently represents an alkyl, alkylphenyl, alkoxyphenyl, or halogenated phenyl group.)

Specific examples of the cyanine compound of the present invention represented by general formula (I) include Compounds No. 1 to 27 below. Examples illustrated below are given as a cyanine cation without an anion.

[Formula 4]

Compound No. 1

Compound No. 2

Compound No. 3

Compound No. 4

Compound No. 5

Compound No. 6

Compound No. 7

-continued

Compound No. 8

Compound No. 9

[Formula 5]

Compound No. 10

Compound No. 11

-continued

Compound No. 12

Compound No. 13

Compound No. 14

Compound No. 15

-continued

Compound No. 16

Compound No. 17

Compound No. 18

[Formula 6]

Compound No. 19

-continued

Compound No. 20

Compound No. 21

Compound No. 22

Compound No. 23

-continued

Compound No. 24

Compound No. 25

Compound No. 26

Compound No. 27

Among the cyanine compounds, for the reason of still better thermal behavior as optical recording materials, preferred are the ones in which the ring composing the indole skeleton with the optionally substituted benzyl group (ring A in general formula (I)) is a naphthalene ring (for example, Compounds No. 1 to 12, 19 to 22, and 24 to 27), particularly the ones in which a benzene ring is condensed with the e-bond of the indole ring (for example, Compounds No. 1 to 4, 7 to 12, 19 to 22, and 25 to 27); and the ones in which ring B in general formula (I) is a benzene ring (for example, Compounds No. 1 to 18, 20, 21, and 23 to 27). More preferred are the ones in which ring A is a naphthalene ring and ring B is a benzene ring (for example, Compounds No. 1 to 12, 20, 21, and 24 to 27). Supposedly, this effect results from strain of the ring system due to steric hindrance between the optionally substituted benzyl group and the benzoindole ring.

The cyanine compound of the present invention represented by general formula (I) is not limited according to the manufacturing method. The cyanine compound can be obtained, for example, by reacting intermediates, a 2-methylthiazolium salt derivative and a 2-methylindole quaternary salt derivative, with a bridging agent such as N,N'-diphenylformamidine. The optionally substituted benzyl group can be introduced in the course of preparing the 2-methylindole quaternary salt derivative as an intermediate. The optionally substituted benzyl group may be introduced when forming indole ring starting from an arylhydrazine derivative with using a 2-butanone derivative whose 4-position is substituted with a phenyl group optionally having substituent X1 or may be introduced by reacting the indole ring with a benzyl halide derivative. Y1 and Y2 can be introduced using Y1-D and Y2-D, respectively, (D being a halogen atom such as chlorine, bromine, and iodine; or a sulfonyloxy group such as phenylsulfonyloxy, 4-methylphenylsulfonyloxy, and 4-chlorophenylsulfonyloxy) reactive to the NH group in an arylamine derivative or an indole ring. The 2-butanone derivatives whose 4-position is substituted with the phenyl group optionally having substituent X1 can be readily obtained by reacting acetone with a benzaldehyde optionally having substituent X1. One example of the specific strategy to obtain the cyanine compounds of the present invention is the route represented by [Formula 7] below:

[Formula 7]

(In the formula, ring A, ring B, R2, $Y_1$, $Y_2$, X, $X_1$, and m are the same as those in general formulae (I) and (II). $An_1^-$, $An_2^-$, and $An^-$ indicate anions.)

The cyanine compound of the present invention functions as an optical element and is particularly suitable for optical recording layers of optical recording media. The optical recording layer containing the cyanine compound of the present invention is formed as a thin film on a substrate using an optical recording material containing the cyanine compound of the present invention. The optical recording material of the present invention encompasses the cyanine compound of the present invention itself as well as mixtures of the cyanine compound(s) of the present invention and organic solvent(s) and/or various compounds described hereinafter.

A method to form the optical recording layer of optical recording media using the optical recording material of the present invention is not particularly limited. There is generally adopted a wet coating method in which the cyanine compound of the present invention and various compounds described hereinafter as needed are dissolved in an organic solvent to prepare a solution, which is applied to a substrate by spin coating, spraying, dip coating, or the like. The solvent used here includes lower alcohols such as methanol and ethanol; ether alcohols such as methyl cellosolve, ethyl cellosolve, butyl cellosolve, and butyl diglycol; ketones such as acetone, methyl ethyl ketone, methyl isobutyl ketone, cyclohexanone, and diacetone alcohol; esters such as ethyl acetate, butyl acetate, and methoxyethyl acetate; acrylates such as ethyl acrylate and butyl acrylate; fluoroalcohols such as 2,2,3,3-tetrafluoropropanol; hydrocarbons such as benzene, toluene, and xylene; chlorohydrocarbons such as dichloromethane, dichloroethane, and chloroform; and others. Other methods include vapor deposition method, sputtering method, and others.

A suitable thickness of the optical recording layer formed from the optical recording material of the present invention is generally in a range of 0.001 to 10µ, preferably 0.01 to 5µ.

When the optical recording material of the present invention is contained in the optical recording layer of optical recording media, the content of the cyanine compound of the present invention in the optical recording layer is preferably 50 to 100 mass %. In order to form the optical recording layer with such content of the cyanine compound, the optical recording material of the present invention preferably contains 50 to 100 mass % of the cyanine compound of the present invention based on the solid content in the optical recording material of the present invention.

The optical recording layer may contain, besides the cyanine compound(s) of the present invention, as needed, compounds used in optical recording layers such as other cyanine compounds, azo compounds, phthalocyanine compounds, and porphine compounds; resins such as polyethylene, polyester, polystyrene, and polycarbonate; surfactants; antistatic agents; lubricants; flame retardants; radical scavengers such as hindered amines; pit-formation accelerators such as ferrocene derivatives; dispersants; antioxidants; crosslinkers; light fastness contributors; and others. The optical recording layer may further contain aromatic nitroso compounds, ammonium compounds, iminium compounds, bisiminium compounds, transition metal chelate compounds, or the like as a quencher of singlet oxygen or the like.

Such various compounds are preferably used in a range of 0 to 50 mass % in the optical recording layer. To that end, the optical recording material of the present invention preferably contains 0 to 50 mass % of these compounds based on the solid content in the optical recording material of the present invention.

There is no particular limitation on the material of the substrate on which the optical recording layer is formed so far as it is substantially transparent to writing (recording) light and reading (play-back) light. Examples thereof include resins such as polymethyl methacrylate, polyethylene terephthalate, and polycarbonate, glass, and others. The substrate may be in any form such as tape, drum, belt, and disc, according to the application.

On the optical recording layer, there may be formed a reflective film with gold, silver, aluminum, copper, or the like by vapor deposition or sputtering, and there may be also formed a protective layer with an acrylic resin, ultraviolet-curing resin or the like.

The optical recording material of the present invention is suitable for optical recording media on which recording and play-back are performed with a semiconductor laser, particularly for optical discs such as high-speed recordable DVD-R.

EXAMPLES

The present invention will be described in more detail in accordance with Examples and Evaluation Examples. However, the present invention is not limited by Examples and the like below.

Example 1

Preparation of Hexafluorophosphate of Compound No. 2

Into a reaction flask were charged 2.9 g (0.005 mol) of indole derivative A represented by [Formula 8] below, 2.0 g (0.005 mol) of intermediate B obtained via the synthetic route shown in [Formula 9] below, and 4.2 g (0.05 mol) of pyridine, and the content was heated to 40° C. and stirred to make homogeneous. Here was added dropwise 0.8 g (0.0075 mol) of acetic anhydride, and the reaction was conducted for 4 hours. After cooling, the reaction mixture was washed with 40 g of chloroform/30 g of water twice, treated with an aqueous solution containing 3 g (0.015 mol) of potassium hexafluorophosphate twice for ion exchange, and washed twice with water. After the solvent was removed with an evaporator, 35 g of methanol was added to the residue to precipitate crystals. The solid was collected by filtration, washed with methanol, and dried under vacuum to give 2.6 g (yield: 74%) of grey solid. The grey solid obtained was confirmed to be the target substance (hexafluorophosphate of Compound No. 2). The analytical results are shown below.

[Formula 8]

Indole derivative A

-continued

[Formula 9]

Synthetic route of Intermediate B

Intermediate B

Analytical results

Optical properties (chloroform, $1.01 \times 10^{-6}$ mol/l) $\lambda_{max}$: 584 nm, $\epsilon$: $1.2 \times 10^5$ Endothermic temperature (endothermic peak top in TG/DTA measurement at heating speed of 10° C./min under nitrogen) 213.1° C.

Molecular weight (Time-of-flight mass spectrometry) 660.7

$^1$H-NMR (solvent: DMSO)

Figure 1:
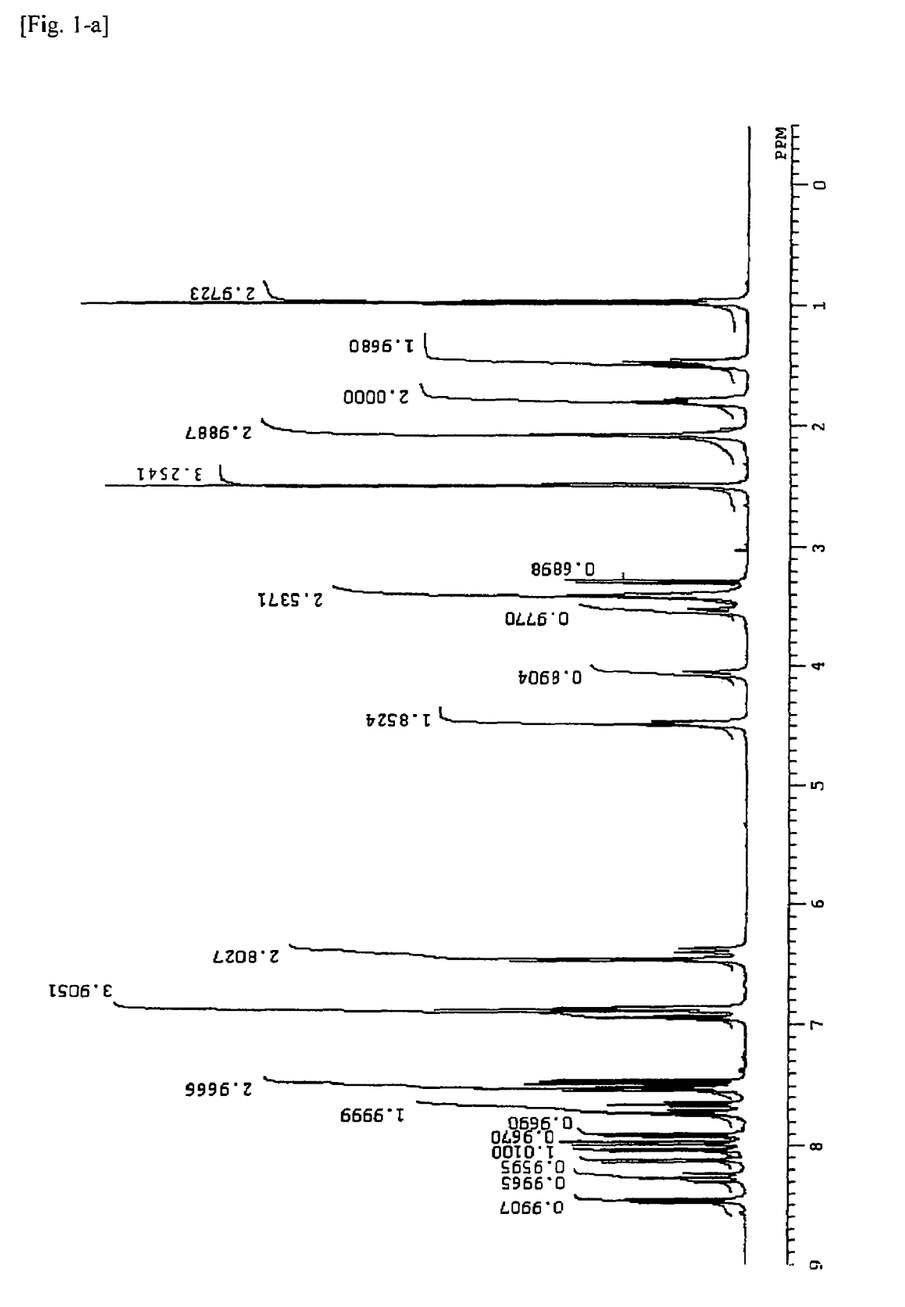

The $^1$H-NMR spectrum is shown in FIG. 1.

Example 2

Preparation of Hexafluorophosphate of Compound No. 8

Into a reaction flask were charged 16.5 g of indole derivative A, 8.7 g (0.03 mol) of intermediate C represented by [Formula 10], and 47.4 g (0.6 mol) of pyridine. The content was stirred, here was added dropwise 4.6 g (0.045 mol) of acetic anhydride at ambient temperature, and the reaction was conducted for 15 hours. The reaction mixture was washed with 150 g of chloroform/100 g of water twice, treated with an aqueous solution containing 5.5 g (0.03 mol) of potassium hexafluorophosphate once for ion exchange, washed twice with water. The solvent was removed with an evaporator to give a crude product. The resultant crude product was purified with column-chromatography (eluted with ethyl acetate:hexane=1.5:1, substances remained on column top was extracted with methanol), and the eluate was concentrated to yield 1.8 g of purple solid, which was recrystallized from dimethylacetamide/methanol to give 1.3 g (yield: 7%) of purple solid. The purple solid obtained was confirmed to be the target substance (hexafluorophosphate of Compound No. 8). The analytical results are given below.

[Formula 10]

Intermediate C

Analytical results

Optical properties (chloroform, $9.81 \times 10^{-6}$ mol/l) $\lambda_{max}$: 547 nm, $\epsilon$: $1.14 \times 10^5$ Endothermic temperature (endothermic peak top in TG/DTA measurement at heating speed of 10° C./min under nitrogen) 218.4° C.

Molecular weight (Time-of-flight mass spectrometry) 616.6

$^1$H-NMR (solvent: DMSO)

Figure 2:
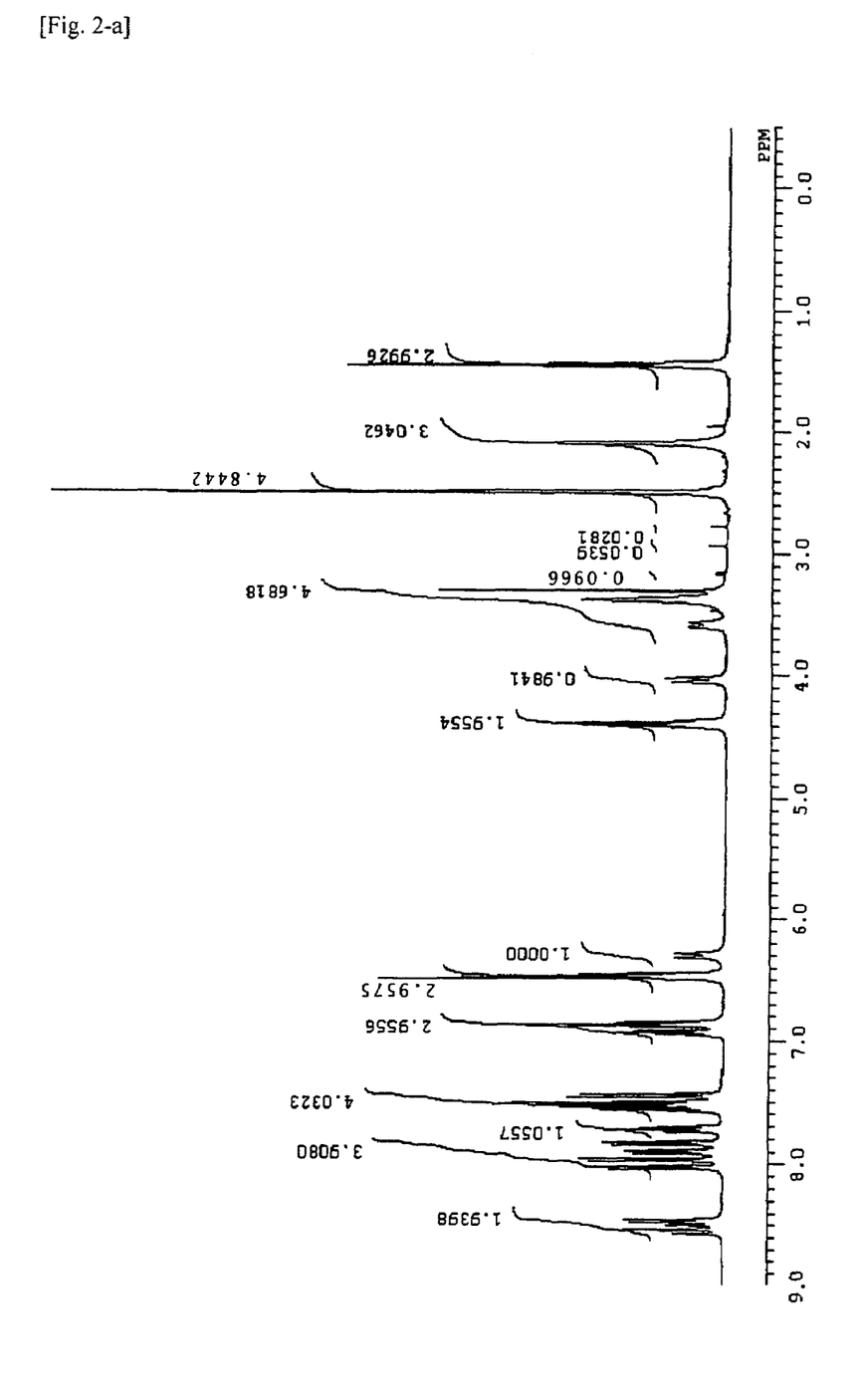

The $^1$H-NMR spectrum is shown in FIG. 2.

Evaluation Example 1

Compounds No. 2 and 8 obtained in Examples above and Comparative Compound 1 represented by [Formula 11] below were subjected to differential thermal analysis under nitrogen to determine the thermal decomposition temperature. The thermal decomposition temperature refers to the temperature at an exothermic peak top in DTA at a heating speed of 10° C./min under nitrogen. The results are shown in Table 1.

TABLE 1

[Formula 11]

Comparative Compound No. 1

| Cyanine compound | | Thermal decomposition |
|---|---|---|
| Cation | Anion | temperature (° C.) |
| Compound No. 2 | PF$_6^-$ | 192.8 |
| Compound No. 8 | PF$_6^-$ | 232.5 |
| Comparative Compound No. 1 (anion: PF$_6^-$) | | 276.7 |

The results in Table 1 confirm that the cyanine compounds of the present invention have lower thermal decomposition temperature. This indicates the cyanine compounds of the present invention are suitable for high-speed recording as optical recording materials.

Example 3

Hexafluorophosphate of Compound No. 2 was dissolved in 2,2,3,3-tetrafluoropropanol to adjust the concentration to 1 mass % to prepare an optical recording material. A polycarbonate disc substrate with a diameter of 12 cm was coated with a titanium chelate compound (T-50 from Nippon Soda Co., Ltd.) and then hydrolyzed to form an undercoat layer (0.01 μm). To this substrate, the optical recording material was applied by spin coating (spinning at a revolution of 2000 rpm for 1 min) to fabricate an optical recording medium. When the transmission-mode UV spectrum of this optical recording medium was measured, $\lambda_{max}$ was appeared at 598 nm, confirming that the optical recording material is suitable as an optical recording material for DVD-R.

Example 4

Similarly to Example 3, an optical recording material was prepared and an optical recording medium was prepared using the optical recording material, except that hexafluorophosphate of Compound No. 2 was replaced with hexafluorophosphate of Compound No. 8. When the transmission-mode UV spectrum of this optical recording medium was measured, $\lambda_{max}$ was appeared at 558 nm, confirming that the optical recording material is suitable as an optical recording material for DVD-R.

INDUSTRIAL APPLICABILITY

The present invention can provide new cyanine compounds exhibiting thermal behavior more suitable for use in optical recording, an optical recording material containing the compound, and an optical recording media using the optical recording material.

The invention claimed is:

1. An optical recording medium comprising an optical recording layer coated upon a substrate together with a reflective layer or a UV cured protective layer, wherein the recording layer comprises a cyanine compound having a decomposition temperature of less than 192.8 degrees C. and represented by general formula (I) below:

[Formula 1]

pAn$^{m-}$ wherein each of ring A and ring B represents an optionally substituted benzene or naphthalene ring; each of R1 and R2 independently represents an alkyl group having 1 to 4 carbon atoms or an optionally substituted benzyl group; at least one of R1 and R2 is an optionally substituted benzyl group; X represents S; each of Y, $Y_1$, and $Y_2$ independently represents a hydrogen atom or an organic group having 1 to 30 carbon atoms; Z represents a hydrogen atom, a halogen atom, or a cyano group; An$^{m-}$ represents an m-valent anion; m represents an integer of 1 or 2; and p represents a coefficient to keep an electric charge neutral.

2. The optical recording medium according to claim 1, wherein ring B in the general formula (I) is a benzene ring.

3. The optical recording medium according to claim 2, wherein ring A in the general formula (I) is a naphthalene ring.

4. The optical recording medium according to claim 2, wherein each of $Y_1$ and $Y_2$ in the general formula (I) is an alkyl group having 1 to 8 carbon atoms.

5. The optical recording medium according to claim 2, wherein either R1 or R2 in the general formula (I) is a methyl group.

6. The optical recording medium according to claim 1, wherein ring A in the general formula (I) is a naphthalene ring.

7. The optical recording medium according to claim 6, wherein each of $Y_1$ and $Y_2$ in the general formula (I) is an alkyl group having 1 to 8 carbon atoms.

8. The optical recording medium according to claim 1, wherein each of $Y_1$ and $Y_2$ in the general formula (I) is an alkyl group having 1 to 8 carbon atoms.

9. The optical recording medium according to claim 1, wherein either R1 or R2 in the general formula (I) is a methyl group.

* * * * *